(12) United States Patent
Lho et al.

(10) Patent No.: US 9,855,354 B2
(45) Date of Patent: Jan. 2, 2018

(54) APPARATUS FOR MEDICAL STERILIZATION USING PLASMA

(75) Inventors: Tai Hyeop Lho, Daejeon (KR); Dong Chan Seok, Daejeon (KR)

(73) Assignee: KOREA BASIC SCIENCE INSTITUTE, Daejeon (KR)

( * ) Notice: Subject to any disclaimer, the term of this patent is extended or adjusted under 35 U.S.C. 154(b) by 80 days.

(21) Appl. No.: 14/123,152

(22) PCT Filed: Jun. 4, 2012

(86) PCT No.: PCT/KR2012/004383
§ 371 (c)(1),
(2), (4) Date: Feb. 11, 2014

(87) PCT Pub. No.: WO2012/165921
PCT Pub. Date: Dec. 6, 2012

(65) Prior Publication Data
US 2014/0241953 A1    Aug. 28, 2014

(30) Foreign Application Priority Data

Jun. 3, 2011 (KR) .................. 10-2011-0054024

(51) Int. Cl.
*A61L 2/14* (2006.01)
*H05H 1/46* (2006.01)
*A61L 2/20* (2006.01)

(52) U.S. Cl.
CPC .............. *A61L 2/14* (2013.01); *A61L 2/208* (2013.01); *H05H 1/46* (2013.01); *A61L 2202/11* (2013.01);
(Continued)

(58) Field of Classification Search
CPC ..................................... A61L 2/14
(Continued)

(56) References Cited

U.S. PATENT DOCUMENTS 5,084,239 A    1/1992  Moulton et al.
5,087,418 A *  2/1992  Jacob ................. A61L 2/14
                                                          204/164

(Continued)

FOREIGN PATENT DOCUMENTS

CN        1658909 A    8/2005
CN      200957198 Y   10/2007
(Continued)

OTHER PUBLICATIONS

European Patent Office, European Search Report of European Patent Application No. 12792482.7, dated Nov. 26, 2014.

*Primary Examiner* — Kevin Joyner
*Assistant Examiner* — Holly M Mull
(74) *Attorney, Agent, or Firm* — IP Legal Services, LLC

(57) ABSTRACT

The present invention relates to an apparatus for sterilization which may be applied to a medical dry sterilizer, and more particularly, to an apparatus which injects hydrogen peroxide so as to generate plasma and OH radicals which are effective in sterilization, so as to achieve the sterilization of a treated object. According to the present invention, the apparatus for sterilization comprises: a sterilizing reactor in which sterilization is performed on a treated object; a vacuuming unit which is equipped with a vacuum pump connected to the sterilizing reactor and which vacuumizes the interior of the sterilizing reactor; a hydrogen-peroxide supply unit which supplies hydrogen peroxide in a gas state to the interior of the sterilizing reactor; and a microwave-plasma generating unit which generates plasma using microwaves. The microwave-plasma generating unit is provided with an electromagnetic-wave generating source which generates microwaves; a plasma-generating unit which interconnects the hydrogen-peroxide supply unit and the sterilizing reactor such that hydrogen peroxide is supplied to the sterilizing reactor, and which generates plasma using micro- (Continued)

waves; and a microwave guide which delivers the microwaves generated from the electromagnetic-wave generating source to the plasma-generating unit.

3 Claims, 4 Drawing Sheets

(52) U.S. Cl.
CPC .. *A61L 2202/24* (2013.01); *H05H 2001/4622* (2013.01); *H05H 2245/1225* (2013.01)

(58) Field of Classification Search
USPC .......................................................... 422/292
See application file for complete search history.

(56) References Cited

U.S. PATENT DOCUMENTS

| | | | |
|---|---|---|---|
| 5,244,629 A | 9/1993 | Caputo et al. | |
| 5,325,020 A * | 6/1994 | Campbell et al. | ....... 315/111.21 |
| 5,413,758 A | 5/1995 | Caputo et al. | |
| 5,620,656 A | 4/1997 | Wensky et al. | |
| 5,645,796 A | 7/1997 | Caputo et al. | |
| 6,261,518 B1 | 7/2001 | Caputo et al. | |
| 6,274,058 B1 * | 8/2001 | Rajagopalan | ....... C23C 16/4405 134/22.1 |
| 6,342,187 B1 * | 1/2002 | Jacob et al. | ............. 422/186.05 |
| 7,824,610 B2 | 11/2010 | Ko | |
| 2004/0005261 A1 | 1/2004 | Ko | |
| 2004/0120869 A1 | 6/2004 | Ko | |
| 2005/0271564 A1 | 12/2005 | Ko | |
| 2010/0254853 A1 * | 10/2010 | Lee et al. | ........................ 422/29 |
| 2011/0005461 A1 * | 1/2011 | Vandermeulen | ...... 118/723 MA |
| 2011/0008207 A1 | 1/2011 | Arai et al. | |
| 2012/0192953 A1 | 8/2012 | Matsushima | |

FOREIGN PATENT DOCUMENTS

| | | |
|---|---|---|
| EP | 0 474 137 A2 | 3/1992 |
| JP | 60-116456 U | 8/1985 |
| JP | 62-28838 U | 2/1987 |
| JP | 62-028838 U | 2/1987 |
| JP | 63-089162 A | 4/1988 |
| JP | 05-242995 A | 9/1993 |
| JP | 05-317390 A | 12/1993 |
| JP | 2003-250868 A | 9/2003 |
| JP | 2003-310720 A | 11/2003 |
| JP | 2004-160168 A | 6/2004 |
| JP | 2005-279042 A | 10/2005 |
| JP | 2009-110802 A | 5/2009 |
| JP | 2011-029475 A | 2/2011 |
| KR | 10-2000-0008420 A | 2/2000 |
| KR | 20-0303495 Y1 | 2/2003 |
| KR | 10-2003-0084585 A | 11/2003 |
| KR | 10-0913632 B1 | 8/2009 |
| WO | 02/22447 A1 | 3/2002 |
| WO | 2004/041316 A1 | 5/2004 |

* cited by examiner

[Fig. 1]
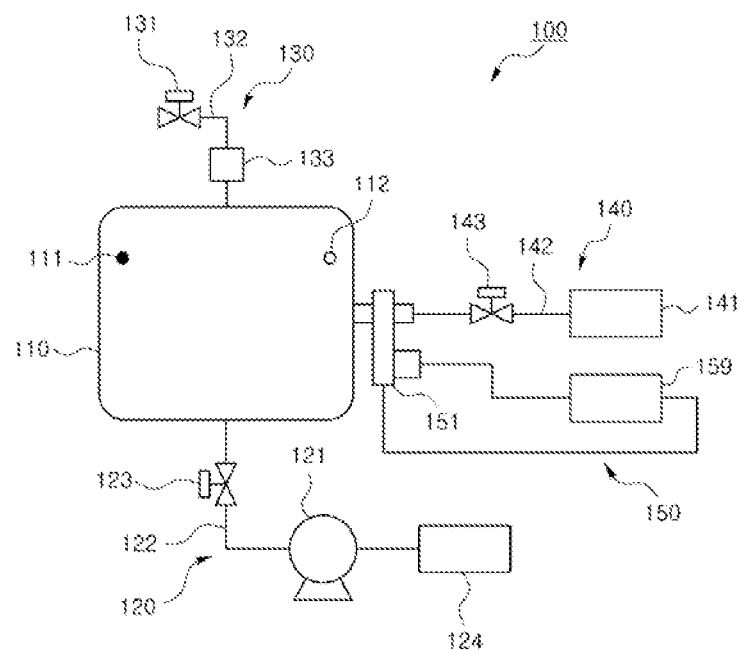

[Fig. 2]
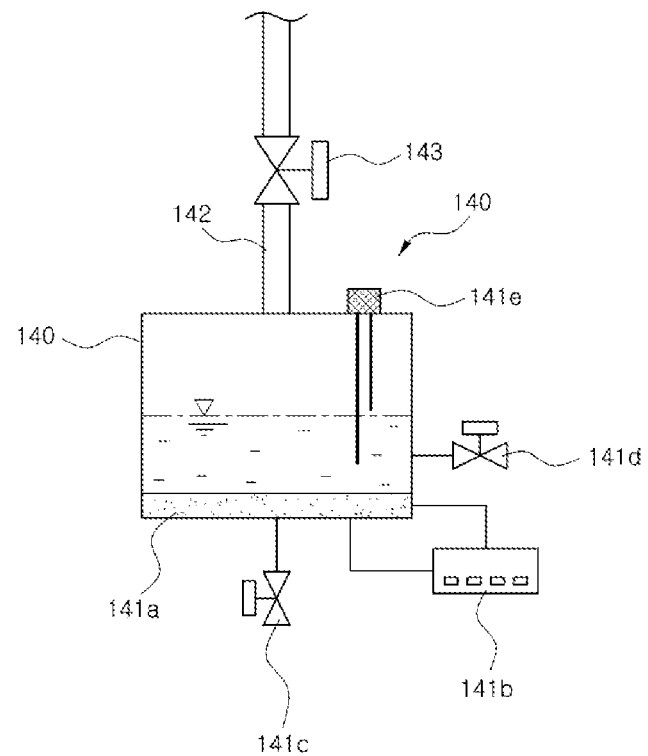
[Fig. 3]
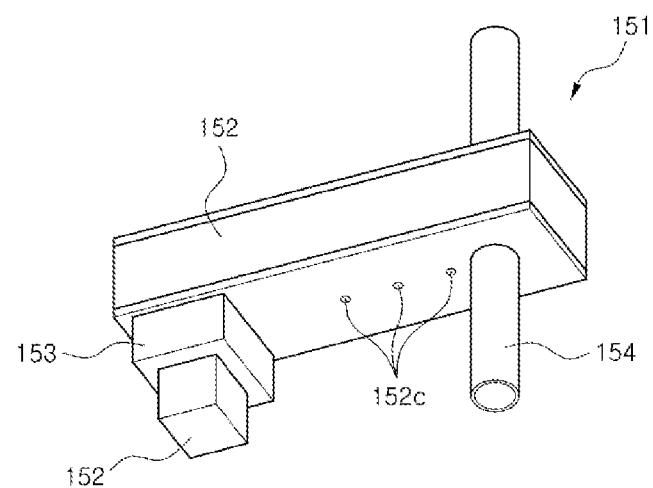

[Fig. 4]
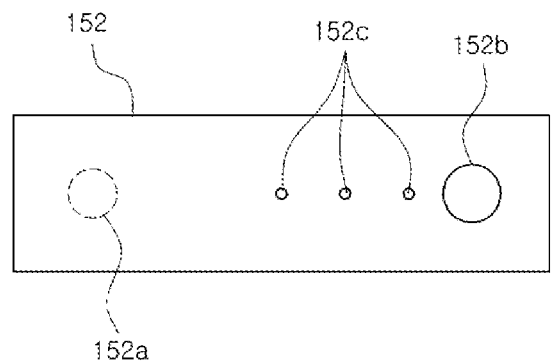
[Fig. 5]
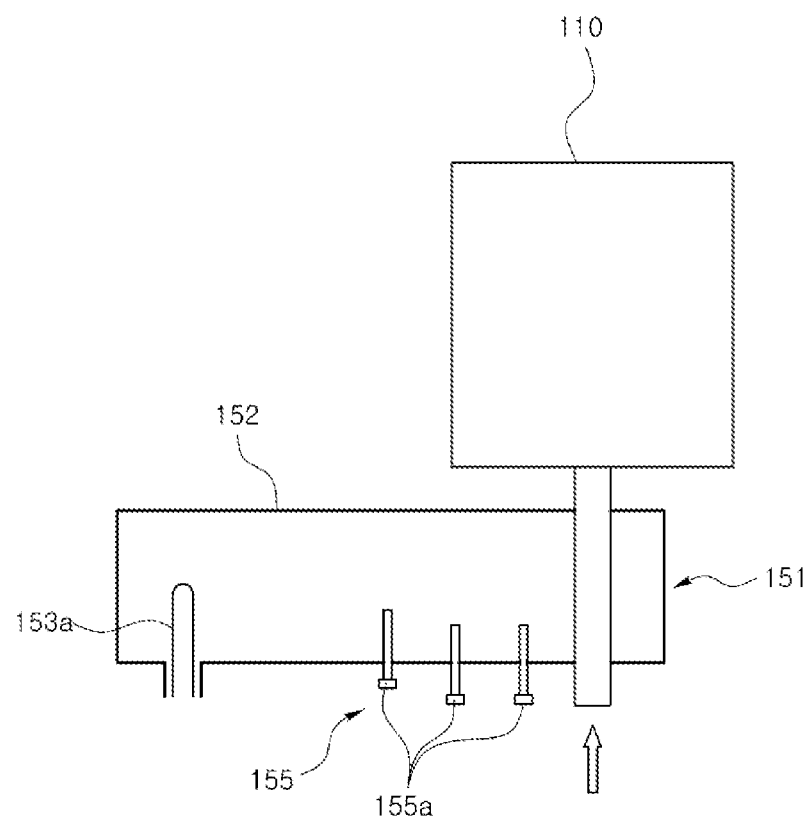

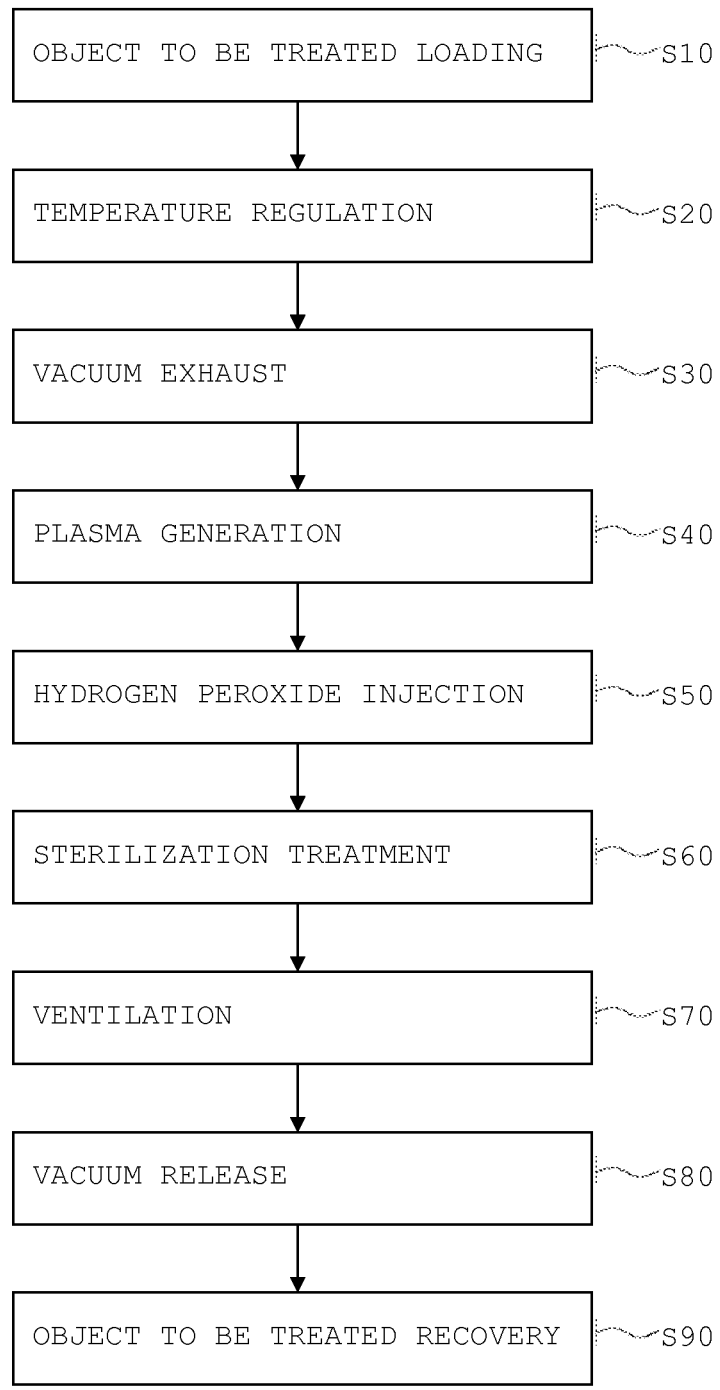
[Fig. 6]

APPARATUS FOR MEDICAL STERILIZATION USING PLASMA

CROSS REFERENCE TO RELATED APPLICATIONS

This application is a National Stage Patent Application of PCT International Patent Application No. PCT/KR2012/004383 (filed on Jun. 4, 2012) under 35 U.S.C. §371, which claims priority to Korean Patent Application No. 10-2011-0054024 (filed on Jun. 3, 2011), the teachings of which are incorporated herein in their entireties by reference.

TECHNICAL FIELD

The present invention relates to a sterilization apparatus applicable to a medical dry sterilizer, and more particularly, to an apparatus capable of achieving sterilization of an object to be treated by injecting hydrogen peroxide to generate plasma and OH radicals which are effective in sterilization.

BACKGROUND ART

In general, there are used a method using ETO (Ethylene Oxide) gas, a method using ozone and water, a method using hot steam, and the like in order to sterilize a medical device. The ETO contact method has an excellent sterilization effect. However, since ETO gas is highly toxic, the ETO gas does harm to user's health and is difficult to treat. The method using ozone and water requires a long treatment time. The sterilization method using hot steam has a short sterilization time and an excellent sterilization effect, but may not be used for an object which is weak to heat.

Recently, a sterilization device using plasma and hydrogen peroxide is developed and has satisfactory sterilization performance. However, such a device uses a high-priced power supply and is costly.

DISCLOSURE

Technical Problem

Accordingly, the present invention has been made in view of the above-mentioned problems, and an object thereof is to provide an apparatus for medical sterilization using plasma, capable of being used for an object to be treated having a material which is weak to heat and shortening a treatment time for sterilization while achieving a reduction in manufacturing costs.

Technical Solution

In accordance with an aspect of the present invention, an apparatus for medical sterilization using plasma includes a sterilization reactor to perform sterilization treatment on an object to be treated, a vacuum forming unit which includes a vacuum pump connected to the sterilization reactor and vacuumizes the inside of the sterilization reactor, a hydrogen peroxide supply unit which provides gaseous hydrogen peroxide supplied into the sterilization reactor, and a microwave plasma generation unit to generate plasma using microwaves, wherein the microwave plasma generation unit includes an electromagnetic wave generation source to generate microwaves, a plasma generation portion which connects the hydrogen peroxide supply unit to the sterilization reactor such that hydrogen peroxide is supplied to the sterilization reactor and in which plasma is generated by microwaves, a microwave guide which transfers the microwaves generated by the electromagnetic wave generation source to the plasma generation portion.

The plasma generation portion may have a tube shape or a cup shape made of a dielectric material.

The plasma generation portion may be formed in double tubes such that a cooling fluid flows between the two tubes.

The microwave guide may have a tubular shape closed at both ends thereof, and the electromagnetic wave generation source and the plasma generation portion may be installed so as to be spaced apart from each other in a longitudinal direction of the microwave guide.

Vacuum exhaust may be performed through the plasma generation portion by the vacuum forming unit.

Advantageous Effects

In accordance with the present invention, the foregoing object of the present invention may be completely achieved. Specifically, the present invention provides a sterilization apparatus which is reusable after use of a medical device, a sterilization apparatus which is usable even for sterilization of the medical device made of a material easily deformable by heat, a relatively low-priced sterilization apparatus using hydrogen peroxide plasma, a sterilization apparatus having a short sterilization time, a sterilization apparatus which has a simple structure and is easily usable, and a sterilization apparatus which enables sterilization even when outdoor air temperature is less than 30° C. In addition, plasma is generated by a microwave generator and is mainly generated in a region of an object to be treated instead of periphery thereof, enabling the object to be treated to come into contact with generated radicals.

Additional advantages, objects, and features of the invention will be set forth in part in the description which follows and in part will become apparent to those having ordinary skill in the art upon examination of the following or may be learned from practice of the invention.

BRIEF DESCRIPTION OF DRAWINGS

The above and other objects, features and other advantages of the present invention will be more clearly understood from the following detailed description taken in conjunction with the accompanying drawings.

FIG. 1 is a diagram schematically illustrating a configuration of an apparatus for medical sterilization using plasma according to an embodiment of the present invention which uses hydrogen peroxide and microwaves.

FIG. 2 is a diagram schematically illustrating a configuration of a hydrogen peroxide supply unit shown in FIG. 1.

FIG. 3 is a perspective view illustrating a microwave plasma generator shown in FIG. 1.

FIG. 4 is a top view illustrating a microwave transfer member shown in FIG. 3.

FIG. 5 is a view schematically illustrating a state of connecting a sterilization reactor to the microwave plasma generator shown in FIG. 3.

FIG. 6 is a flowchart illustrating a method of sterilizing a medical device by means of the apparatus for medical sterilization using plasma shown in FIG. 1.

BEST MODE FOR INVENTION

It should be understood that the following specific structural and functional descriptions are merely examples given for the purpose of providing a description of the exemplary embodiments according to the concept of the present invention. Accordingly, various variations may be performed on the exemplary embodiments of the present invention, and it should be understood that the scope and spirit of the present invention will not be limited only to the exemplary embodiments presented in the description of the present invention set forth herein.

Since various variations may be performed on the exemplary embodiments according to the concept of the present invention and the embodiments of the present invention can be realized in a wide range of varied forms, specific exemplary embodiments of the present invention will be described herein in detail with reference to the appended drawings of the exemplary embodiments of the present invention. However, the present invention will not be limited only to the specific exemplary embodiments of the present invention which are disclosed herein. Therefore, it should be understood that the scope and spirit of the present invention can be extended to all variations, equivalents, and replacements in addition to the appended drawings of the present invention.

Furthermore, the terms including expressions, such as first and/or second, used in the specification of the present invention may be used to describe various elements of the present invention. However, the elements of the present invention should not be limited by the terms used in the specification of the present invention. In other words, such terms will be used only to differentiate one element from other elements of the present invention. For example, without deviating from the scope and spirit of the present invention, a first element may be referred to as a second element, and, similarly, a second element may also be referred to as a first element.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Other expressions for describing relationships between elements, for example, "between" and "immediately between" or "neighboring" and "directly neighboring" may also be understood likewise.

The terminology used in the specification of the present invention is for the purpose of describing particular embodiments only and is not intended to limit the invention. As used in the specification and the appended claims, the singular forms "a", "an" and "the" are intended to include the plural forms as well, unless context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms, including technical and scientific terms, used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

An apparatus for medical sterilization using plasma according to the present invention which uses hydrogen peroxide and microwaves has the following features.

It may be possible to obtain a high electric field by establishing standing waves in a state of holing microwaves in a cavity such as a waveguide, thereby enabling plasma to be generated at particular gas. Microwave plasma may have high electron temperature and plasma density and may be maintained at a pressure condition of a wide range (e.g. 5~15 eV, $10^8$~$10^{15}$ $cm^{-3}$, unmagnetized: 10 mTorr~760 torr, magnetized: few μtorr~10 mTorr), compared with typical DC or RF plasma.

In addition, it may be possible to achieve a relatively high ionization rate and minimize damage of an electrode or a structure by sputtering because of having low sheath voltage.

In accordance with the present invention, it may be possible to generate plasma by installing a proper waveguide to an electromagnetic wave source (a magnetron or the like), which may generate microwaves, and installing a dielectric load to one tip thereof so as to create the inside of the dielectric load as proper pd (pressure×distance). In this case, when hydrogen peroxide is present in the generated plasma, substances such as OH radicals required for sterilization are generated by electron collision, UV absorption, molecule-atom collision, and the like.

When plasma is generated at a condition in which hydrogen peroxide is present, cells or spores such as bacteria may be sterilized by the generated UV and become extinct by direct collision between electrons having high energy and gas particles. It is the most important to generate high oxidative chemicals such as OH radicals or $HO_2$ radicals depending upon decomposition of hydrogen peroxide and accelerate a sterilization reaction.

Since plasma may be generated at a low temperature condition, an object to be treated having a material such as resin which is weak to heat may be sterilized and a medical device having a fine and complicated structure may be applied according to adjustment of pressure.

In addition, since a plasma generation portion is spaced apart from an object to be treated, it may be possible to prevent failure of the medical device by an electric shock.

Reference will now be made in detail to embodiments of the present invention, examples of which are illustrated in the accompanying drawings. The same reference numbers will be used throughout the drawings to refer to the same or like parts.

Referring to FIG. 1, an apparatus for medical sterilization using plasma 100 includes a sterilization reactor 110, a vacuum forming unit 120, an outdoor air supply unit 130, a hydrogen peroxide supply unit 140, and a microwave plasma generation unit 150.

The sterilization reactor 110 is a reactor to perform sterilization treatment on a medical device which is an object to be treated. The sterilization reactor 110 includes a temperature sensor 111 to measure temperature within the sterilization reactor 110, a pressure sensor 112 to measure pressure within the sterilization reactor 110, and a heater (not shown) to control temperature of the sterilization reactor 110 and the object to be treated. Although not shown, the sterilization reactor 110 is provided with an openable and closable operation door, a vacuum exhaust port, an ozone supply port, a hydrogen peroxide supply port, and an outdoor air supply port. A degree of vacuum less than about 100 mTorr has to be ensured within the sterilization reactor 110, and internal volume thereof is calculated according to the purpose of use if necessary.

The vacuum forming unit 120 includes a vacuum pump 121, a first connection pipe 122, and a first adjustment valve 122. The vacuum forming unit 120 vacuumizes the inside of the sterilization reactor 110. The vacuum pump 121 discharges gas within the sterilization reactor 110 to the outside. The vacuum pump 121 preferably has durability against hydrogen peroxide. The first connection pipe 122 connects the vacuum pump 121 to the vacuum exhaust port (not shown) provided in the sterilization reactor 110. The first adjustment valve 122 is installed on the first connection pipe 122 to open and close the first connection pipe 122. Exhaust gas passing through the vacuum pump 121 is finally discharged via an oxidant removal device 124.

The outdoor air supply unit 130 includes a second adjustment valve 131, a second connection pipe 132, and a heater 133. The outdoor air supply unit 130 supplied outdoor air to the sterilization reactor 110 as occasion demands. The second adjustment valve 131 is installed on the second connection pipe 132 to open and close the second connection pipe 132. The second connection pipe 132 is connected to the outdoor air supply port (not shown) provided in the sterilization reactor 110. The heater 133 is installed on the second connection pipe 132 so as to be adjacent the outdoor air supply port (not shown), and controls temperature in the sterilization reactor 110.

Referring to FIGS. 1 and 2, the hydrogen peroxide supply unit 140 includes a hydrogen peroxide vaporizer 141, a third connection pipe 142, and a third adjustment valve 143. The hydrogen peroxide supply unit 140 supplies vaporized hydrogen peroxide into the sterilization reactor 110. The hydrogen peroxide vaporizer 141 is provided therein with a storage space in which hydrogen peroxide is stored, and includes a heater 141a, a temperature regulator 141b, a drainage valve 141c, a feed valve 141d, and a level sensor 141e. The heater 141a serves to prevent liquid hydrogen peroxide from being cooled and frozen due to excessive evaporation. The temperature regulator 141b controls operation of the heater 141a. The drainage valve 141c is used to discharge liquid hydrogen peroxide stored in the hydrogen peroxide vaporizer 141. The feed valve 141d is used to supply liquid hydrogen peroxide into the hydrogen peroxide vaporizer 141. An amount of liquid hydrogen peroxide stored in the hydrogen peroxide vaporizer 141 is measured by the level sensor 141e. Hydrogen peroxide used in the hydrogen peroxide vaporizer 141 has a concentration of 1 to 100%. On the other hand, hydrogen peroxide may also be supplied to the sterilization reactor 110 by a spraying method, an ozone diffusion method, etc. The hydrogen peroxide vaporizer 141 may evaporate liquid hydrogen peroxide having a concentration of 3 to 100% such that the hydrogen peroxide is evaporated and supplied by an amount less than that corresponding to the saturated pressure of 100% in the internal volume of the sterilization reactor 110 at a preset temperature of the sterilization reactor 110.

The third connection pipe 142 connects the hydrogen peroxide vaporizer 141 to the microwave plasma generation unit 150. The third connection pipe 142 preferably has a temperature regulation function or a heat insulation function. The third adjustment valve 143 is installed on the third connection pipe 142 to open and close the third connection pipe 142.

Referring to FIGS. 1 and 3 to 5, the microwave plasma generation unit 150 includes a microwave plasma generator 151 and a power supply 159. The microwave plasma generation unit 150 generates plasma using microwaves.

The microwave plasma generator 151 includes an electromagnetic wave generation source 153, a microwave guide 152, a plasma generation portion 154, and a tuner portion 155.

The electromagnetic wave generation source 153 generates microwaves. A microwave is an electromagnetic wave having a frequency of 0.3 to 300 GHz and is used in the fields of military radars, household cookers, wireless communication, etc. Since the microwave has the same band as the rotational frequency of water molecule, the microwave has a characteristic of being absorbed into water to heat water molecule. In addition, it is reported that power may also be transported to a long distance by the microwave. Although a magnetron is described as being used as the electromagnetic wave generation source 153 in the present embodiment, the present invention is not limited thereto. The electromagnetic wave generation source 153 includes an antenna 153a. The electromagnetic wave generation source 153 is powered by the power supply 159.

The microwave guide 152 has a tubular shape closed at both ends thereof and has a square shape in section. The microwave guide 152 is provided with the electromagnetic wave generation source 153 and the plasma generation portion 154 which are spaced apart from each other in a longitudinal direction thereof. The antenna 153a of the electromagnetic wave generation source 153 is located in an inner space of the microwave guide 152. The microwave guide 152 transfers microwaves generated by the electromagnetic wave generation source 153 to the plasma generation portion 154. The microwave guide 152 includes an electromagnetic wave generation source installation hole 152a formed corresponding to an installation position of the electromagnetic wave generation source 153, and a plasma generation portion installation hole 152b formed corresponding to an installation position of the plasma generation portion 154. A plurality of tuner installation holes 152c, which are sequentially located in the longitudinal direction of the microwave guide 152, are formed between the electromagnetic wave generation source installation hole 152a and the plasma generation portion installation hole 152b.

The plasma generation portion 154 has a tube shape (or a cup shape) made of a dielectric material and is installed to the plasma generation portion installation hole 152b so as to pass through the inner space of the microwave guide 152. The plasma generation portion 154 is connected, at one end thereof, to the sterilization reactor 110 while being connected, at the other end thereof, to the third connection pipe 142 of the hydrogen peroxide supply unit 140, with the consequence that hydrogen peroxide gas is supplied to the sterilization reactor 110 via the plasma generation portion 154. Plasma is generated in the inside of the plasma generation portion 154 by microwaves. Consequently, hydrogen peroxide passing through the inside of the plasma generation portion 154 is decomposed so that high oxidative chemicals such as OH radicals or $HO_2$ radicals to accelerate a sterilization reaction are generated. The plasma generation portion 154 may be formed in double tubes such that a cooling fluid (oil, compressed air, or the like) flows between the double tubes.

The tuner portion 155 includes a plurality of tuning members 155a. The tuning members 155a have a rod shape and are respectively coupled to the tuner installation holes 152c formed on the microwave guide 152, for example, by a screw method. Each of the tuning members 155a has a length protruding into the inner space of the microwave guide 152 while the length is adjusted. Three tuning members 155a are provided in the present embodiment.

When moisture is present in an object to be treated and there is a high temperature difference, it may be required to equally maintain the temperature of the object to be treated and the ambient temperature of the object to be treated. In this case, it may be possible to open the first adjustment valve 131 and purge air outside the sterilization reactor 110 to be conditioned. In addition, it may also be possible to supply heated air using the heater 133.

Hereinafter, a detailed description will be given of a method of sterilizing a medical device by means of the apparatus for medical sterilization using plasma shown in FIG. 1 with reference to FIG. 6. Referring to FIG. 6, a method of sterilizing a medical device includes an object to be treated loading step (S10), a temperature regulation step (S20), a vacuum exhaust step (S30), a plasma generation step (S40), a hydrogen peroxide injection step (S50), a sterilization treatment step (S60), a ventilation step (S70), a vacuum release step (S80), and an object to be treated recovery step (S90).

At the object to be treated loading step (S10), a medical device which is an object to be treated is loaded within the sterilization reactor 110 (see FIG. 1) in a state in which the apparatus for medical sterilization using plasma shown in FIG. 1 is not operated.

At the temperature regulation step (S20), the temperature in the sterilization reactor is properly maintained such that vaporized hydrogen peroxide supplied from the hydrogen peroxide supply unit 140 (see FIG. 1) is not condensed within the sterilization reactor 110 (see FIG. 1).

At the vacuum exhaust step (S30), vacuum exhaust is performed such that the inside of the sterilization reactor 110 (see FIG. 1) reaches 10 torr or less using the vacuum forming unit 120, enabling sterilization agents to be evenly infiltrated into a microstructure of the object to be treated.

At the plasma generation step (S40), plasma is generated in the plasma generation portion 154 (see FIG. 3) by operation of the microwave plasma generation unit 150 (see FIG. 1). After hydrogen peroxide is injected, the plasma may be continuously generated within a range of sixty minutes or less. The generation of the plasma is completed before ventilation with respect to the sterilization reactor, or is completed after ventilation with respect to the sterilization reactor continues when vacuum exhaust progresses to pass through the plasma generation portion.

At the hydrogen peroxide injection step (S50), the hydrogen peroxide vaporized by the hydrogen peroxide supply unit 140 (see FIG. 1) is injected into the sterilization reactor 110 (see FIG. 1) via the plasma generation portion 154 (see FIG. 3).

At the sterilization treatment step (S60), sterilization treatment is performed on the medical device in the sterilization reactor 110 (see FIG. 1).

At the ventilation step (S70), vacuum exhaust is performed such that the inside of the sterilization reactor 110 (see FIG. 1) reaches the pressure less than 10 torr. The vacuum exhaust may progress to pass through the plasma generation portion 154 (see FIG. 3). In this case, it may be possible to prevent remaining hydrogen peroxide from being discharged to the outside by changing non-reacted hydrogen peroxide into water and oxygen.

At the vacuum release step (S80), the vacuum state formed within the sterilization reactor 110 (see FIG. 1) via the ventilation step (S70) is released.

At the object to be treated recovery step (S90), the sterilization-treated object is recovered.

If necessary, the plasma generation step (S40) to the ventilation step (S70) may also be repeated two times or more.

Various embodiments have been described in the best mode for carrying out the invention. Although the present invention has been described with respect to the illustrative embodiments, it will be apparent to those skilled in the art that various variations and modifications may be made without departing from the spirit and scope of the invention as defined in the following claims.

What is claimed is:
1. An apparatus for medical sterilization using plasma, comprising:
 a sterilization reactor configured to perform sterilization treatment on an object to be treated;
 a vacuum forming unit which comprises a vacuum pump connected to the sterilization reactor and is configured to vacuumize the inside of the sterilization reactor;
 a hydrogen peroxide supply unit configured to provide gaseous hydrogen peroxide supplied into the sterilization reactor; and
 a microwave plasma generation unit configured to generate plasma using microwaves,
 wherein the microwave plasma generation unit comprises:
  an electromagnetic wave generation source configured to generate the microwaves,
  a plasma generation portion which connects the hydrogen peroxide supply unit to the sterilization reactor such that the gaseous hydrogen peroxide is supplied from the hydrogen peroxide supply unit to the sterilization reactor and in which the plasma is generated by the microwaves, and
  a microwave guide which is configured to transfer the microwaves generated by the electromagnetic wave generation source to the plasma generation portion and has a plurality of holes for coupling with the plasma generation portion;
 wherein the plasma generation portion is configured to pass through an inner space of the microwave guide through the plurality of holes, wherein one end of the plasma generation portion is connected to the hydrogen peroxide supply unit and the other end of the plasma generation portion is connected directly to the sterilization reactor such that a non-circular flow path is formed;
 wherein at least a part, located in the inner space of the microwave guide, of the plasma generation portion is entirely formed in a double tube structure including an inner tube without perforations and an outer tube without perforations such that a cooling fluid flows through a space between the inner tube and the outer tube, wherein the inner and outer tubes are made of a dielectric material such that the microwaves are transferred to an inner space of the inner tube and the plasma is generated by the transferred microwaves in the inner space of the inner tube of the plasma generation portion;
 wherein the gaseous hydrogen peroxide supplied to the inner tube of the plasma generation portion passes through a plasma region in the inner tube of the plasma generation portion; and
 wherein the vacuum forming unit includes a connection unit connecting the vacuum pump to the plasma generation portion such that a remaining gas inside the sterilization reactor is discharged through the plasma generation portion when a vacuum exhaust operation is performed after the sterilization treatment on the object.

2. The apparatus according to claim 1, wherein the microwave guide has a tubular shape closed at both ends thereof, and the electromagnetic wave generation source and the plasma generation portion are installed so as to be spaced apart from each other in a longitudinal direction of the microwave guide.

3. The apparatus according to claim 1, wherein the microwave plasma generation unit includes:
   at least one antenna which is configured to transmit the generated microwaves and is located in an inner space of the microwave guide.

\* \* \* \* \*